United States Patent [19]

Franzmair

[11] 4,142,051
[45] Feb. 27, 1979

[54] ARYLAMINOIMIDAZOLINE DERIVATIVES

[75] Inventor: Rudolf Franzmair, Linz-Ebelsberg, Austria

[73] Assignee: Chemie Linz Aktiengesellschaft, Austria

[21] Appl. No.: 898,543

[22] Filed: Apr. 20, 1978

[30] Foreign Application Priority Data

Mar. 17, 1978 [DE] Fed. Rep. of Germany ....... 2811847

[51] Int. Cl.$^2$ ............................................ C07D 233/50
[52] U.S. Cl. .............................. 548/315; 424/273 R; 548/320
[58] Field of Search ......................................... 548/315

[56]       References Cited
        U.S. PATENT DOCUMENTS

| 3,799,921 | 3/1974 | Zellerhoff et al. | 548/315 |
| 3,804,833 | 4/1974 | Stähle et al. | 548/315 |
| 3,931,216 | 1/1976 | Franzmair | 548/315 |
| 3,988,345 | 10/1976 | Franzmair | 548/315 |

FOREIGN PATENT DOCUMENTS 741947  5/1970  Belgium .................................. 548/315

OTHER PUBLICATIONS

Franzmair, Chem. Abst., 1976, vol. 84, No. 84:180214p.

Primary Examiner—Natalie Trousof
Attorney, Agent, or Firm—Wenderoth, Lind & Ponack

[57] ABSTRACT

Novel Arylaminoimidazoline derivatives of the formula

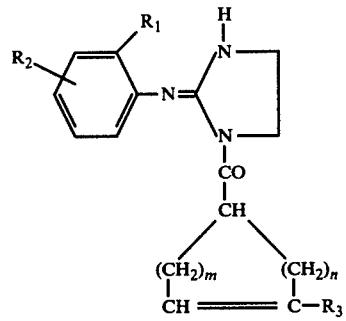

in which $R_1$ and $R_2$ are chlorine, bromine or an alkyl group with 1 to 4 C atoms, $R_3$ is hydrogen or an alkyl radical with 1 – 4 C atoms and n and m each represent an integer from 1 to 3, the sum of n + m being an integer from 2 to 5 inclusive, and their salts. This novel compounds have a pronounced analgesic action.

11 Claims, No Drawings

ARYLAMINOIMIDAZOLINE DERIVATIVES

It is known that arylaminoimidazolines, in particular 2,6-dichlorophenylamino-2-imidazoline (clonidine) have a pronounced, hypotensive action, which is coupled with a sedative action. Moreover, some of these compounds also have a more or less pronounced analgesic action which, however, because of the simultaneous existence of the hypotensive action and the depressant action on the central nervous system, was considered unexploitable. (In this context see the work of R. D. E. Sewell and P. S. J. Spencer, Progress in Medicinal Chemistry, 14, 1977, page 254). It is also stated there that certain derivatives of phenylaminoimidazoline, for example clonidine which is substituted on the aniline N by an allyl group, exhibit a more favorable relationship of analgesic to hypotensive action than clonidine itself, but in this case also the other pharmacological actions are still too highly pronounced. A hypotensive action has also been described for benzoyl derivatives of arylaminoimidazolines, especially for the compound 1-benzoyl-2-(2',6'-dichlorophenylamino)-2-imidazoline, in U.S. Pat. No. 3,988,345, the depressant action on the central nervous system and thus the sedative action being substantially less pronounced with this compound.

Surprisingly, it has been found that arylaminoimidazoline derivatives of the general formula

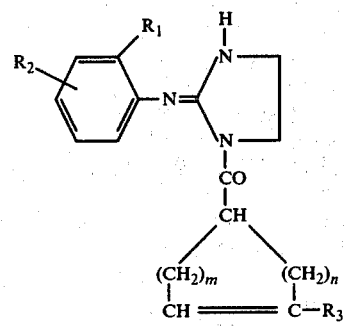

in which $R_1$ and $R_2$ denote halogen atoms or an alkyl group with 1 to 4 C atoms, $R_3$ denotes a hydrogen atom or an alkyl radical with 1 to 4 C atoms and n and m each represent an integer from 1 to 3, with the proviso that the sum $n + m$ is a number from 2 to 5 inclusive, and the acid addition salts of these compounds, have a pronounced analgesic action, whilst virtually no action on the blood pressure, be it a lowering or increase, or action on the central nervous system, occurs. This is all the more surprising, since the compounds of the formula I, above all those in which $n + m$ denotes the number 3, so that they are cyclohexenoyl derivates, differ only in the degree of saturation of the six-membered ring of the acyl radical from the benzoyl derivatives according to U.S. Pat. No. 3,988,345, in which the blood pressure-lowering action is particularly pronounced, the depressant action on the central nervous system is very slight and the relationship of analgesic action to hypotensive action is greatly shifted in favor of the hypotensive action.

The powerful analgesic action of the compounds of the formula I can be seen in chemical pain tests, for example in the suppression of the writhing syndrome caused by intraperitoneal injection of 0.3 ml of a 0.02% strength solution of phenylquinone in a mixture of alcohol and water. It can, however, also be detected in the so-called hot-plate test in mice. In both test methods the long period of action of the compounds according to the invention is striking. Thus, for example, in the hot-plate test in mice, using the substance 1-(cyclohex-3"-en-1"-oyl)-2-(2',6'-dichlorophenylamino)-2-imidazoline, after administering 1 or 2 mg/kg subcutaneously a significant analgesic effect can still be detected 60 minutes after the administration, and after administering 5–10 mg/kg perorally a significant analgesic effect can still be detected 90 minutes after the administration.

The action on the blood pressure was determined, for example, in anaesthetized rats after intravenous administration into the jugular vein, a slight fall in blood pressure being recorded with some of the compounds of the formula I and with others, in turn, a slight rise in blood pressure being recorded, but the change being so minimal that therapeutic utilization would not be possible.

The depressant action, which is virtually lacking, on the central nervous system can be detected, for example, by determining the chloral hydrate sleeping time of rats by the method of Laverty and Taylor (Br.J. of Pharmacol. 35 (1969), 253–264).

The compounds of the formula I can therefore advantageously be employed for the treatment of all types of algias, it being possible to administer them orally, enterally or parenterally, either as bases or also in the form of the acid addition salts. They can, of course, be combined with other active compounds, such as, for example, spasmolytic agents, tranquilizers and the like.

Compounds of the formula I with 2 Cl atoms in the phenyl nucleus exhibit a good action.

Particularly preferred compounds of the formula I are, above all, those which are substituted in the 2-position and 6-position of the aniline radical, the 2,6-dichloro compounds and the 2-chloro-6-methyl compounds in turn being preferred. Acyl radicals which may be mentioned are, in particular, cyclohex-3-enoyl or 4-methyl-cyclohex-3-enoyl radicals; however, compounds of the formula I which contain cyclopent-3-enoyl and cyclohept-4-enoyl radicals also show favorable actions. Examples of compounds with a very powerful analgesic action and only a very slight action, which can be ignored when used in practice, on the blood pressure and on the central nervous system are 1-(cyclohex-3"-en-1"-oyl)-2-(2',6'-dichlorophenylamino)-2-imidazoline, 1-(cyclohex-3"-en-1"-oyl)-2-(2'-chloro-6'-methylphenylamino)-2-imidazoline, 1-(cyclohex-3"-en-1"-oyl)-2-(2',3'-dichlorophenylamino)-2-imidazoline, 1-(cyclohex-3"-en-1"-oyl)-2-(2'-methyl-3'-chlorophenylamino)-2-imidazoline, 1-(4"-methyl-cyclohex-3"-en-1"-oyl)-2-(2',6'-dichlorophenylamino)-2-imidazoline, 1-(cyclohept-4"-en-1"-oyl)-2-(2',6'-dichlorophenylamino)-2-imidazoline and 1-(cyclopent-3"-en-1"-oyl)-2-(2',6'-dichlorophenylamino)-2-imidazoline.

The compounds of the formula I are manufactured by reacting an aniline derivative of the general formula

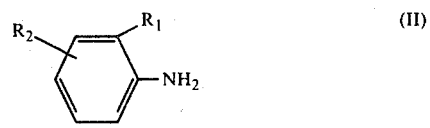

in which $R_1$ and $R_2$ are as defined above, with a 1-acylimidazolidine-2-one of the general formula

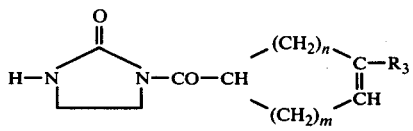

in which $R_3$, n and m are as defined in formula I in the presence of at least 2 equivalents of phosphorus oxychloride and, after separating off the excess phosphorus oxychloride, the reaction product formed is subjected to mild hydrolysis.

However, it is also possible to obtain the compounds of the formula I by reacting 2-arylamino-2-imidazolines of the general formula

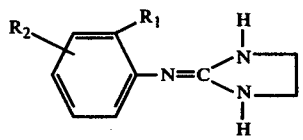

in which $R_1$ and $R_2$ are defined as indicated above, with an acid derivative of the formula

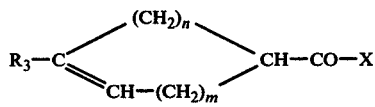

in which $R_3$, n and m are defined as indicated above and X represents the radical of a hetero-aromatic, five-membered ring containing at least two nitrogen atoms, a hetero-aromatic, five-membered ring which is fused with a benzene nucleus and contains at least two nitrogen atoms, a radical of the formula

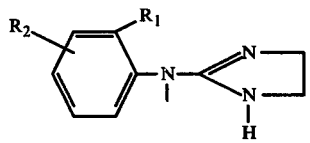

in which $R_1$ and $R_2$ are as defined above or an acid radical of the formula

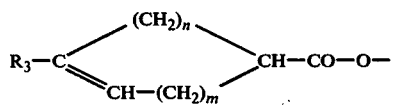

in which $R_3$, n and m are as defined above. The resulting compounds of the formula I can be isolated as free bases or as acid addition salts.

The reaction of the anilines of the formula II with the 1-acylimidazolidine-2-one of the formula III can be carried out in inert, organic solvents, such as halogenated hydrocarbons, but preferably in phosphorus oxychloride itself, at temperatures between room temperature and the boiling point of the chosen solvent. A reaction temperature of 50° to 80° C. is preferred here.

After the reaction, the phosphorus oxychloride present in excess is distilled off and can be reused again without further purification.

The residue obtained after removing the phosphorus oxychloride is a phosphorus-containing intermediate product which is split by mild hydrolysis, the desired product of the formula I being formed. This mild hydrolysis can preferably be carried out by taking up the evaporation residue in an inert, water-immiscible solvent, for example in methylene chloride, chloroform, carbon tetrachloride, aromatic hydrocarbons or ether. The P-containing intermediate product is decomposed by adding ice-water, after which the aqueous, acid phase is neutralized by adding a base, such as, for example, alkaline earth metal carbonates, alkaline earth metal bicarbonates, sodium hydroxide solution, potassium hydroxide solution or ammonia. Here it is necessary to ensure that a relatively strong alkaline reaction is not produced. The pH value of the aqueous phase should preferably be between 7 and 8. The desired end product of the formula I can then be isolated from the organic phase by evaporation. It is, however, just as easily possible to carry out the reaction without an organic solvent. In this case, the evaporation residue is decomposed directly with ice-water, after which the acid solution formed is neutralized or rendered very weakly alkaline in order to obtain the base. This procedure is advisable above all if the compound of the formula I to be prepared is able to crystallize out of the aqueous phase.

The starting materials of the formula III are obtained by reacting imidazolidin-2-one with the corresponding carboxylic acid chloride in a polar solvent, for example acetonitrile.

If compounds of the formula IV are used as starting materials for the manufacture of the compounds of the formula I, the reaction with the compounds of the formula V is preferably carried out in an organic medium, it being possible to use either polar or non-polar solvents. Examples of such solvents which can be used are aromatic hydrocarbons, such as benzene, toluene or xylene, ethers, such as tetrahydrofuran, diethyl ether and dioxan, esters, such as ethyl acetate, halogenated hydrocarbons, such as methylene chloride, chloroform or carbon tetrachloride, ketones, such as, for example acetone or methyl ethyl ketone, and aprotic, polar solvents, such as, for example, acetonitrile, dimethylformamide or dimethylsulfoxide.

The compounds of the formula V can be either active amides or anhydrides. Active amides which can be used are, above all, azolides, which are derived from imidazole, 1,2,4-triazole, tetrazole, benzimidazole or benztriazole. X in formula V can, however, also denote the group

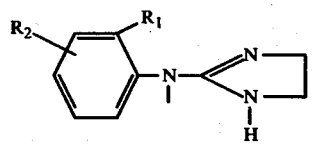

If the substituents $R_1$ and $R_2$ of the benzene nucleus are identical in this formula VI and in the compound of the formula IV to be acylated, it is not necessary to employ the compound of the formula IV in equimolar amounts, or in an only slightly less than equimolar amount, relative to the compound of the formula V employed. Rather, it suffices in this case to use an amount of the compound of the formula IV which is considerably less than the equivalent amount, appropriately less than half an equivalent, preferably even only one tenth of an equivalent, relative to the active amide of the formulae V, since the compound of the formula IV is of course continuously liberated from the active amide of the formula V in the course of the acylation. This variant of the process according to the invention is preferably carried out by boiling the starting materials in an aprotic, inert solvent, such as, for example, toluene or xylene.

If the compound of the formula V is an acid anhydride, it is possible to carry out the reaction not only in an organic medium, but also in an aqueous, weakly alkaline medium. The reaction at room temperature is particularly advantageous here.

If the reaction is carried out in an anhydrous medium, for example in anhydrous tetrahydrofuran, it has proved advantageous to add an acid-binding agent, for example an amine, such as triethylamine.

The working up takes a very simple form in the case of all the variants for the manufacture of the compounds according to the invention in which the compounds of the formula IV are used as starting materials. The evaporation residue which remains after the solvent has been evaporated off can be simply purified by recrystallization. In some cases it is advisable first to digest the dry residue with water, whereupon crystallization starts.

If the reaction is carried out with compounds of the formula V in which X represents the radical of a heteroaromatic, five-membered ring which contains at least two N atoms and can be fused to benzene, that is to say is carried out with an azolide, it is not necessary in all cases to manufacture this azolide of the formula V in a separate operation. Azolides of the formula V can also be produced in situ from the corresponding azole and an acid chloride of the formula

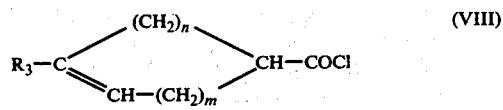

(VIII)

and can be further used direct. It is thus possible, for example, to react acid chlorides of the formula VIII with imidazole in tetrahydrofuran, and, after the reaction has ended and the azole hydrochloride has been filtered off, to introduce a solution of the compound of the formula IV into the reaction solution. An azolide of the formula V can also be prepared in situ by reacting the acid of the formula

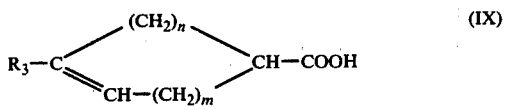

(IX)

with N,N'-carbonyldiimidazole.

Active amides in which X represents the group of the formula VI can be obtained by reacting compounds of the formula IV with the acid chlorides of the formula VIII.

The compounds of the formula I can be isolated as free bases or, after being converted into acid addition salts, as their salts. Suitable salts here are, above all, salts of strong mineral acids, such as hydrogen halides, sulfates, cyclohexylsulfamates and the like.

The compounds of the formula I and their acid addition salts can be used orally, enterally or also parenterally. They can also be administered in combination with other active compounds, such as other analgesics, spasmolytic agents, tranquilizers and the like. Examples of suitable galenical forms for administration are tablets, dragées, capsules, suppositories, solutions, emulsions or powders; the galenical auxiliaries, excipients, disintegrating agents or lubricants and substances for producing a depot action which are customarily used can be employed for their preparation. Galenical forms for administration, of this type, are prepared in the conventional manner by known methods.

The examples which follow illustrate the invention without limiting it.

EXAMPLE 1

8.1 g (50 mmoles) of 2,6-dichloroaniline, 10.67 g (55 mmoles) of 1-cyclohex-3'-en-1'-oyl-imidazolidin-2-one and 100 ml of phosphorus oxychloride are stirred at 50° C. for 70 hours. The excess phosphorus oxychloride is removed in vacuo, about 500 ml of ice-water are added to the residue and the mixture is stirred at room temperature for one hour. A saturated solution of potassium bicarbonate is then added until the pH remains at 7, whereupon crystals start to separate out. The mixture is filtered and the crystals are dried. 16.7 g (98.8% of theory) of crude 1-(cyclohex-3''-en-1''-oyl)-2-(2',6'-dichlorophenylamino)-2-imidazoline are obtained. The crude product is recrystallized from isopropanol and 13.77 g (81.5% of theory) of analytically pure product of melting point 159°–162° C. are obtained.

5 g of the 1-(cyclohex-3''-en-1''-oyl)-2-(2',6'-dichlorophenylamino)-2-imidazoline thus obtained are dissolved in 50 ml of anhydrous methylene chloride, and about 4 ml of approximately 20% strength ethereal hydrochloric acid are added. After about ten minutes, crystals separate out of the initially clear solution. The mixture is kept at 0° C. for a further hour, 50 ml of ether are added, the mixture is filtered and the crystals are washed with ether and dried. 5.10 g (92.1% of theory) of 1-(cyclohex-3''-en-1''-oyl)-2-(2',6'-dichlorophenylamino)-2-imidazoline hydrochloride are thus obtained, melting point$_1$ = 180°–187° C., melting point$_2$ = 253°–258° C., with decomposition.

The starting material is prepared by reacting imidazolidin-2-one with cyclohex-3-ene-1-carboxylic acid chloride in the molar ratio 2:1 in acetonitrile at room temperature. 1-(Cyclohex-3'-en-1'-oyl)-imidazolidin-2-one is obtained in a yield of 85.8% of theory. Melting point = 119°–123° C.

EXAMPLE 2

1.62 g (10 mmoles) of 2,6-dichloroaniline, 1.80 g (10 mmoles) of 1-(cyclopent-3'-en-1'-oyl)-imidazolidin-2-one and 20 ml of phosphorus oxychloride are stirred at 80° C. for 20 hours. The excess phosphorus oxychloride is removed in vacuo, the residue which is partially crystalline, is taken up in 50 ml of methylene chloride, 50 ml of ice-water are added and saturated sodium carbonate solution is added, whilst stirring vigorously, until the pH remains at about 7.5 to 8. The organic phase is separated off, the aqueous phase is extracted a further three times with 7 ml of methylene chloride each time and the methylene chloride phases are combined, washed with water until neutral, dried over sodium sulfate and evaporated. The residue is recrystallized from isopropanol, 2.35 g (72.5% of theory) of 1-(cyclopent-3''-en-1''-oyl)-2-(2',6'-dichlorophenylamino)-2-imidazoline being obtained, melting point = 170°–172° C.

The starting material is prepared by reacting imidazolidin-2-one with cyclopent-3-ene-1-carboxylic acid chloride in the molar ratio 2:1 in acetonitrile at room temperature. 1-(Cyclopent-3'-en-1'-oyl)-imidazolidin-2-one is obtained in a yield of 66.7% of theory. Melting point = 166°–169° C.

EXAMPLE 3

0.94 g (5.8 mmoles) of 2,6-dichloroaniline, 1.20 g of 1-(cyclohept-4'-en-1'-oyl)-imidazolidin-2-one and 30 ml of phosphorus oxychloride are stirred at 70° C. for 40 hours.

The excess phosphorus oxychloride is removed in vacuo, the residue is suspended in toluene, ice-water is added and the mixture is worked up as described in Example 2. 2.0 g of a crystalline crude product are obtained, which, after recrystallization from isopropanol, gives 1.60 g (78.43% of theory) of 1-(cyclohept-4''-en-1''-oyl)-2-(2',6'-dichlorophenylamino)-2-imidazoline, melting point = 161°–163° C.

The starting material is obtained by suspending 2 equivalents of imidazolidin-2-one in absolute acetonitrile and adding 1 equivalent of cyclohept-4-ene-1-carboxylic acid chloride dropwise to this suspension at room temperature, whilst stirring. The mixture is stirred at room temperature for 18 hours, the acetonitrile is removed in vacuo, the residue is digested in water and the solid is filtered off, dried and recrystallized from cyclohexane:isopropanol (4:1). 1-(Cyclohept-4'-en-1'-oyl)-imidazolidin-2-one is obtained in 75% yield, melting point = 122°–125° C.

EXAMPLE 4

4.26 g (30 mmoles) of 2-chloro-6-methylaniline, 6.40 g (33 mmoles) of 1-(cyclohex-3'-en-1'-oyl)-imidazolidin-2-one and 60 ml of phosphorus oxychloride are stirred at 60° C. for 69 hours. The mixture is worked up as described in Example 2. The oily residue obtained after evaporating the methylene chloride phases is triturated with 100 ml of 50% strength acetonitrile and the mixture is left at room temperature for some time, whereupon crystallization starts. The mixture is filtered and the crystals are dried and recrystallized from cyclohexane. 7.87 g (82.5% of theory) of 1-(cyclohex-3''-en-1''-oyl)-2-(2'-chloro-6-'-methylphenylamino)-2-imidazoline are thus obtained, melting point = 112°–114° C.

EXAMPLE 5

3.57 g (22 mmoles) of 2,6-dichloroaniline, 4.90 g (23.5 mmoles) of 1-(cyclooct-4'-en-1'-oyl)-imidazolidin-2-one and 100 ml of phosphorus oxychloride are stirred at 90° C. for 20 hours, the mixture is worked up as described in Example 2 and the crude product is recrystallized from isopropanol using active charcoal. 3.01 g (37.17% of theory) of 1-(cyclooct-4''-en-1''-oyl)-2-(2',6'-dichlorophenylamino)-2-imidazoline are thus obtained, melting point = 136°–138° C.

The starting material is obtained by reacting imidazolidin-2-one with cyclooct-4-ene-1-carboxylic acid chloride in the molar ratio 2:1 in absolute acetonitrile at room temperature. 1-(Cyclooct-4'-en-1'-oyl)-imidazolidin-2-one is a viscous, noncrystallizing oil. Its spectra (IR, UV and NMR) are in agreement with the structure indicated.

EXAMPLE 6

1.55 g (22 mmoles) of imidazole are dissolved in 50 ml of absolute tetrahydrofuran, and a solution of 1.57 g (11 mmoles) of cyclohex-3-ene-1-carboxylic acid chloride in 10 ml of absolute tetrahydrofuran is added dropwise to this solution, whilst stirring, and the mixture is stirred at room temperature for 4 hours. The imidazole hydrochloride which has precipitated is filtered off and washed with 5 ml of absolute tetrahydrofurane. A solution of 2.30 g (10 mmoles) of 2-(2',6'-dichlorophenylamino)-2-imidazoline in 15 ml of absolute tetrahydrofurane is added to the filtrate and the mixture is left at room temperature for 20 hours. It is then evaporated in vacuo and the oily residue is triturated with about 50 ml of water, whereupon crystallization starts. The mixture is filtered, and the crystals are washed with water, dried and recrystallized from isopropanol, 3.10 g (91.7% of theory) of 1-(cyclohex-3''-en-1''-oyl)-2-(2',6'-dichlorophenylamino)-2-imidazoline, being obtained, melting point = 159°–162° C.

EXAMPLE 7

1.69 g (5 mmoles) of 2-[N-(cyclohex-3''-en-1''-oyl)-N-(2',6'-dichlorophenyl)-amino]-2-imidazoline and 115 mg (0.5 mmole) of 2-(2',6'-dichlorophenylamino)-2-imidazoline are heated under reflux in 50 ml of absolute toluene for 144 hours. The mixture is then evaporated to dryness in vacuo and the residue is recrystallized from isopropanol, 1.306 g (77.2% of theory) of 1-(cyclohex-3''-en-1''-oyl)-2-(2',6'-dichlorophenylamino)-2-imidazoline being obtained, melting point = 159°–162° C.

The starting material was prepared as follows:

0.54 g (2 mmoles) of tetra-n-butylammonium chloride is dissolved in 30 ml of water, 40 ml of 1 N sodium hydroxide solution are added and a solution of 9.20 g (40 mmoles) of 2-(2',6'-dichlorophenylamino)-2-imidazoline in 40 ml of methylene chloride is added. The mixture is cooled to 0° C. and a solution of 5.73 g (40 mmoles) of cyclohex-3-ene-1-carboxylic acid chloride in 30 ml of methylene chloride is added dropwise, whilst stirring vigorously, and after the dropwise addition has ended, the mixture is stirred at 0° C. for a further 4 hours. Crystals thereby precipitate and are filtered off, washed with methylene chloride/water and dried. 7.75 g of first crystals are thus obtained.

The phases of the filtrate are separated, the aqueous phase is extracted a further 2 times with methylene chloride and the methylene chloride phases are combined, washed with water, dried over sodium sulfate and evaporated. 5.70 g of second crystals are obtained and are combined with the first and recrystallized from isopropanol. 10.80 g (80.0% of theory) of 2-[N-(cyclohex-3''-en-1''-oyl)-N-(2',6'-dichlorophenyl)-amino]-2-imidazoline are obtained, melting point = 218°–220° C.

EXAMPLE 8

1.39 g (11 mmoles) of cyclohex-3-ene-1-carboxylic acid are dissolved in 40 ml of absolute benzene, 1.79 g (11 mmoles) of N,N'-carbonyldiimidazole are added and the mixture is left at room temperature for 1 hour. A solution of 2.10 g (10 mmoles) of 2-(2'-chloro-6'-methylphenylamino)-2-imidazoline in 30 ml of absolute benzene is then added and the mixture is boiled under refulx for 45 minutes. The benzene is removed in vacuo and the oily residue is digested with water, whereupon crystallization starts. The mixture is filtered and the crystals are washed with water, dried and recrystallized from cyclohexane, 2.62 g (82.44% of theory) of 1-(cyclohex-3''-en-1''-oyl)-2-(2'-chloro-6'-methylphenylamino)-2-imidazoline being obtained, melting point = 112°–114° C.

EXAMPLE 9

2.30 g (10 mmoles) of 2-(2',6'-dichlorophenylamino)-2-imidazoline are dissolved in 100 ml of anhydrous tetrahydrofuran, 1.01 g (10 mmoles) of anhydrous triethylamine are added and a solution of 2.34 g (10 mmoles) of cyclohex-3-ene-1-carboxylic acid anhydride (boiling point$_{0.1}$ = 126°–127° C.) in 50 ml of anhydrous tetrahydrofuran are slowly added dropwise to this mixture at room temperature, whilst stirring, and the mixture is further stirred overnight at room temperature. The clear solution is evaporated in vacuo, the residue is taken up in about 50 ml of methylene chloride and the methylene chloride is washed twice with 20 ml of 3% strength sodium bicarbonate solution each time and twice with water and dried over sodium sulfate and evaporated. The crystalline residue is recrystallized from isopropanol, 3.12 g (92.3% of theory) of 1-(cyclohex-3''-en-1''-oyl)-2-(2',6'-dichlorophenylamino)-2-imidazoline being obtained, melting point = 159°–162° C.

The following compounds are obtained in a manner analogous to Examples 1 to 9: 1-(4''-methyl-cyclohex-3''-ene-1''-oyl)-2-(2',6'-dichlorophenylamino)-2-imidazoline, melting point = 152°–154° C., 1-(cyclohex-3''-en-1''-oyl)-2-(2',3'-dichlorophenylamino)-2-imidazoline, melting point = 147°–149° C., 1-(cyclohex-3''-en-1''-oyl)-2-(2'-methyl-3'-chloro-phenylamino)-2-imidazoline, melting point = 112°–115° C. and 1-(cyclohex-3''-en-1''-oyl)-2-(2'-chloro-4'-methyl-phenylamino)-2-imidazoline, melting point 124°–126° C.

What we claim is:

1. An arylaminoimidazoline derivative of the formula

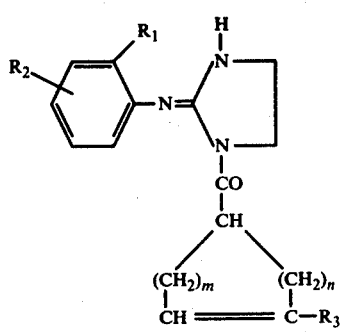

(I)

in which $R_1$ and $R_2$ denote chlorine, bromine or an alkyl group with 1 to 4 C atoms, $R_3$ denotes hydrogen or an alkyl radical with 1–4 C atoms and n and m each represent an integer from 1 to 3, the sum n + m being an integer from 2 to 5 inclusive, and the pharmaceutically acceptable acid addition salts of these compounds.

2. An arylaminoimidazoline derivative according to claim 1, of the formula

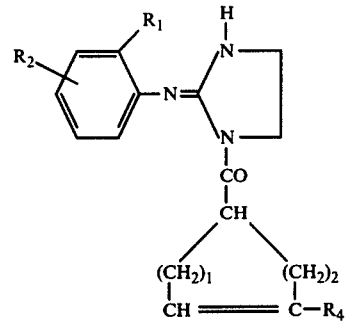

in which $R_1$ and $R_2$ are as defined in claim 1 and $R_4$ represents hydrogen or methyl, and their pharmaceutically acceptable acid addition salts.

3. An arylaminoimidazoline derivative according to claim 1, of the formula

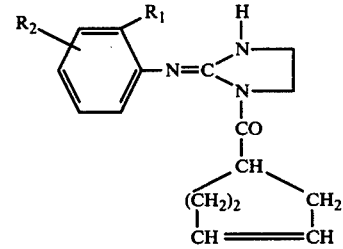

in which $R_1$ and $R_2$ are as defined in claim 1, and their pharmaceutically acceptable acid addition salts.

4. An arylaminoimidazoline derivative according to claim 1, of the formula

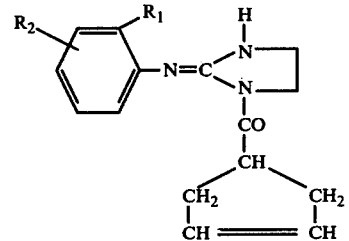

in which $R_1$ and $R_2$ are as defined in claim 1, and their pharmaceutically acceptable acid addition salts.

5. The arylaminoimidazoline derivative 1-(cyclohex-3''-en-1''-oyl)-2-(2',6'-dichlorophenylamino)-2-imidazoline, according to claim 2 and its pharmaceutically acceptable acid addition salts.

6. The arylaminoimidazoline derivative 1-(cyclohex-3''-en-1''-oyl)-2-(2'-chloro-6'-methylphenylamino)-2-imidazoline, according to claim 2, and its pharmaceutically acceptable acid addition salts.

7. The arylaminoimidazoline derivative 1-(cyclohex-3''-en-1''-oyl)-2-(2',3'-dichlorophenylamino)-2-imidazoline, according to claim 2, and its pharmaceutically acceptable acid addition salts.

8. The arylaminoimidazoline derivative 1-(cyclohex-3''-en-1''-oyl)-2-(2'-methyl-3'-chlorophenylamino)-2-imidazoline, according to claim 2, and its pharmaceutically acceptable acid addition salts.

9. The arylaminoimidazoline derivative 1-(4''-methyl-cyclohex-3''-en-1''-oyl)-2-(2',6'-dichlorophenylamino)-2-imidazoline, according to claim 2, and its pharmaceutically acceptable acid addition salts.

10. The arylaminoimidazoline derivative 1-(cyclohept-4''-en-1''-oyl)-2-(2',6'-dichlorophenylamino)-2-imidazoline, according to claim 3, and its pharmaceutically acceptable acid addition salts.

11. The arylaminoimidazoline derivative 1-(cyclopent-3''-en-1''-oyl)-2-(2',6'-dichlorophenylamino)-2-imidazoline, according to claim 4, and its pharmaceutically acceptable acid addition salts.

* * * * *